US00PP17850P2

(12) United States Plant Patent
Doyle

(10) Patent No.: US PP17,850 P2
(45) Date of Patent: Jul. 3, 2007

(54) ***EURYOPS* PLANT NAMED 'PURFLED'**

(50) Latin Name: *Euryops chrysanthemoides*
Varietal Denomination: Purfled

(75) Inventor: Alice Doyle, Cottage Grove, OR (US)

(73) Assignee: Amerinova Properties, LLC, Bousall, CA (US)

( * ) Notice: Subject to any disclaimer, the term of this patent is extended or adjusted under 35 U.S.C. 154(b) by 0 days.

(21) Appl. No.: 11/299,962

(22) Filed: Dec. 12, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Euryops* plant named 'Purfled', characterized by its compact, upright and rounded plant habit; freely branching habit and short internodes; dense and bushy growth habit; green and pale yellow variegated leaves; continuous flowering habit with numerous inflorescences per plant; and daisy-type inflorescences with bright yellow-colored ray florets and golden yellow-colored disc florets.

1 Drawing Sheet

Botanical designation: *Euryops chrysanthemoides.*
Cultivar denomination: 'Purfled'.

BACKGROUND OF THE INVENTION

The present invention relates to a new and distinct cultivar of *Euryops* plant, botanically known as *Euryops chrysanthemoides* and hereinafter referred to by the cultivar name 'Purfled'.

The new *Euryops* is a naturally-occurring branch mutation of an unnamed selection of *Euryops chrysanthemoides,* not patented. The cultivar Purfled was discovered and selected by the Inventor from within a population of plants of the parent selection in Cottage Grove, Oreg. in November, 2000. The selection of the branch mutation was based on its unique variegated foliage.

Asexual reproduction of the new *Euryops* by terminal cuttings in a controlled environment in Cottage Grove, Oreg. since November, 2000, has shown that the unique features of the *Euryops* are stable and reproduced true to type in successive generations.

SUMMARY OF THE INVENTION

The new *Euryops* has not been observed under all possible environmental conditions. The phenotype may vary somewhat with variations in environment such as temperature and light intensity without, however, any variance in genotype.

The following characteristics have been repeatedly observed and are determined to be basic characteristics of 'Purfled' and distinguish the new *Euryops* as a new and distinct cultivar:

1. Compact, upright and rounded plant habit.
2. Freely branching habit and short internodes; dense and bushy plant habit.
3. Green and pale yellow variegated leaves.
4. Continuous flowering habit with numerous inflorescences per plant.

5. Daisy-type inflorescences with bright yellow-colored ray florets and golden yellow-colored disc florets.

Plants of the new *Euryops* differ from plants of the parent selection primarily in foliage coloration as plants of the parent selection have solid green-colored leaves.

Plants of the new *Euryops* can be compared to plants of the *Euryops* cultivar Viridis, not patented. In side-by-side comparisons conducted in Bonsall, Calif., plants of the new *Euryops* differed primarily from plants of the cultivar Viridis in foliage coloration as plants of the cultivar Viridis have solid green-colored leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Euryops.*

The photograph at the bottom of the sheet comprises a side perspective view of a typical flowering plant of 'Purfled' grown in a container.

The photographs at the top of the sheet comprise close-up views of typical inflorescences of 'Purfled'.

DETAILED BOTANICAL DESCRIPTION

The aforementioned photographs, following observations and averaged measurements describe plants grown in Bonsall, Calif., in an outdoor nursery under full sunlight during the summer with day temperatures ranging from 15° C. to 39° C. and night temperatures ranging from 10° C. to 17° C. Plants were grown in 12.5-cm containers. Plants had been growing for about 18 weeks when the photographs and description were taken. Color references are made to The Royal Horticultural Society Colour Chart, 1995 Edition, except where general terms of ordinary dictionary significance are used.

Botanical classification: *Euryops chrysanthemoides* cultivar Purfled.

Parentage: Naturally-occurring branch mutation of an unnamed selection of *Euryops chrysanthemoides,* not patented.

Propagation:

*Type.*—Terminal vegetative cuttings.

*Time to initiate roots, summer.*—About 15 days at 20° C.

*Time to initiate roots, winter.*—About 20 days at 20° C.

*Time to produce a rooted cutting, summer.*—About five weeks at 20° C.

*Time to produce a rooted cutting, winter.*—About six weeks at 20° C.

*Root description.*—Fine; white in color.

*Rooting description.*—Freely branching; dense.

Plant description:

*General appearance.*—Inverted triangle; compact, upright and rounded plant form with dense foliage, short internodes and inflorescences held above and beyond the foliage; dense and bushy plant habit. Low vigor.

*Plant height.*—About 22 cm.

*Plant width.*—About 18 cm.

*Lateral branch description.*—Quantity per plant: Freely branching with about seven primary lateral branches each with about three secondary lateral branches. Length: About 11 cm. Diameter: About 4 mm. Internode length: Short, about 8 mm. Aspect: Initially upright to outwardly spreading. Texture: Smooth, glabrous. Strength: Very strong. Color: 147C.

*Foliage description.*—Arrangement: Alternate, simple. Length: About 4.8 cm. Width: About 1.2 cm. Shape: Oblanceolate with nine to eleven lobes. Apex: Acute. Base: Attenuate. Margin: Nine to eleven lobes. Texture, upper and lower surfaces: Smooth, glabrous. Venation pattern: Pinnate. Petiole length: About 1 cm. Petiole diameter: About 2 mm. Petiole texture, upper and lower surfaces: Smooth, glabrous. Color: Developing and fully expanded foliage, upper surface: Center, 147B and 147C; towards the margin, 10C; venation, 147B. Developing and fully expanded foliage, lower surface: Center, 147C and 147D; towards the margin, 10C and 10D; venation, 147C. Petiole, upper surface: 147C; towards the margin, 10C. Petiole, lower surface: 147C; towards the margin, 10D.

Inflorescence description:

*Appearance.*—Daisy-type inflorescences with ligulate ray florets. Disc and ray florets develop acropetally on a capitulum. Solitary inflorescences held upright and outwardly on axillary peduncles. Inflorescences positioned perpendicular to the peduncles. Inflorescences persistent.

*Flowering response.*—Under natural conditions, plant flower from spring to early fall in California; plants flower continuous during this period.

*Inflorescence longevity.*—Inflorescences last about one week on the plant.

*Quantity of inflorescences.*—Freely flowering, about 45 open inflorescences and inflorescence buds per plant.

*Fragrance.*—None detected.

*Inflorescence size.*—Diameter: About 4 cm. Depth (height): About 8 mm. Diameter of disc: About 1.2 cm. Receptacle height: About 5 mm. Receptacle diameter: About 1.4 cm.

*Inflorescence buds.*—Height: About 1 cm. Diameter: About 9 mm. Shape: Ovoid. Color: 14B.

*Ray florets.*—Quantity per inflorescence: About 18 arranged in a single whorl. Shape: Ligulate. Length: About 1.2 cm. Width: About 4 mm. Apex: Emarginate. Base: Attenuate. Margin: Entire. Texture, upper and lower surfaces: Smooth, glabrous; longitudinally ridged. Aspect: Initially upright; with development, eventually close to perpendicular to the peduncle with apices slightly recurved. Color: When opening and fully opened, upper surface: 14A. When opening and fully opened, lower surface: 14B.

*Disc florets.*—Arrangement: Massed at the center of the inflorescence. Quantity per inflorescence: Numerous, about 130. Shape: Tubular, elongated; apex, five-pointed; base, fused. Length: About 6 mm. Diameter, apex: About 1 mm. Diameter, base: Less than 1 mm. Color: Immature: 17B. Mature, apex: 17B. Mature, mid-section: 16C. Mature, base: 157A.

*Involucral bracts* (*phyllaries*).—Quantity per inflorescence: About eleven. Length: About 7 mm. Width: About 4 mm. Shape: Elliptic. Apex: Acute. Base: Truncate. Margin: Entire. Texture, upper and lower surfaces: Smooth, glabrous. Color, upper and lower surfaces: Center, 146B; towards the margin, 1C.

*Peduncle.*—Strength: Very strong; stiff. Angle: About 30° to 45° from stem axis. Length: About 14.2 cm. Diameter: About 1 mm. Texture: Smooth, glabrous. Color: 146A.

*Reproductive organs.*—Androecium: Only on disc florets. Stamen quantity per floret: Five. Anther length: About 1 mm. Anther shape: Oblong. Anther color: 17A. Amount of pollen: Scarce. Pollen color: 17A. Gynoecium: Present on ray and disc florets. Pistil quantity per floret: One. Pistil length: About 5 mm. Stigma shape: Two-parted. Stigma color: 13B. Style length: About 2 mm. Style color: 13D. Ovary color: 157A.

*Seed/fruit.*—Seed and fruit production has not been observed.

Disease/pest resistance: Resistance to pathogens and pests common to *Euryops* has not been observed on plants grown under commercial conditions.

Temperature/weather tolerance: Plants of the new *Euryops* have been observed to be tolerant to rain, wind and to temperatures from −5° C. to 40° C.

It is claimed:

1. A new and distinct cultivar of *Euryops* plant named 'Purfled', as illustrated and described.

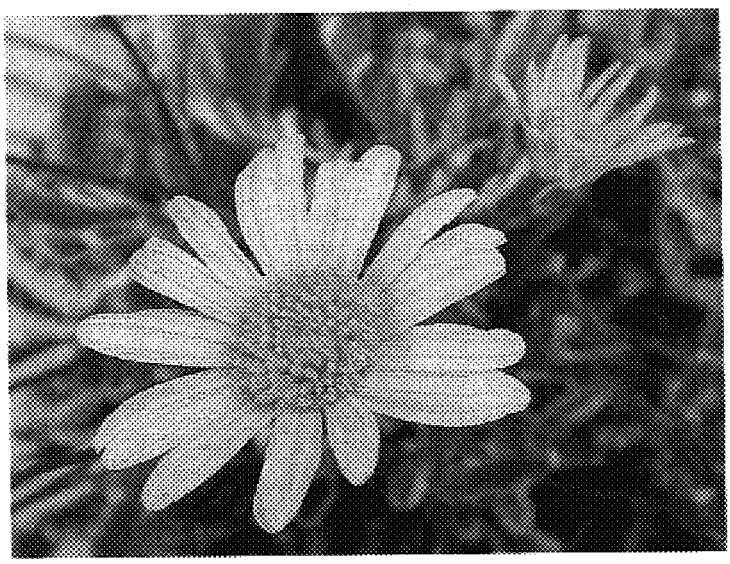
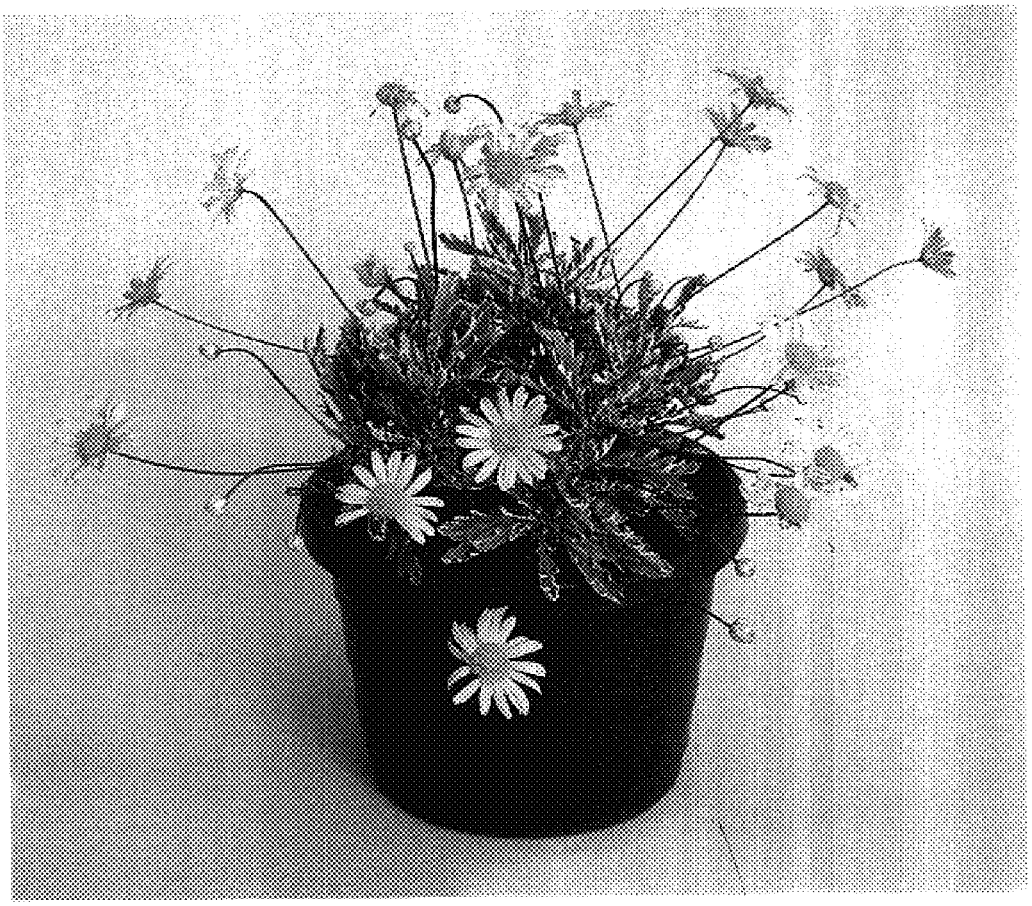

* * * * *